United States Patent
Rommel

(10) Patent No.: US 10,516,536 B2
(45) Date of Patent: Dec. 24, 2019

(54) METHOD AND APPARATUS FOR LOGGING INTO MEDICAL DEVICES

(71) Applicant: SIEMENS HEALTHCARE GMBH, Erlangen (DE)

(72) Inventor: Michael Rommel, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 116 days.

(21) Appl. No.: 15/518,961

(22) PCT Filed: Oct. 12, 2015

(86) PCT No.: PCT/EP2015/073532
§ 371 (c)(1),
(2) Date: Apr. 13, 2017

(87) PCT Pub. No.: WO2016/058976
PCT Pub. Date: Apr. 21, 2016

(65) Prior Publication Data
US 2017/0237565 A1 Aug. 17, 2017

(30) Foreign Application Priority Data
Oct. 14, 2014 (DE) ........................ 10 2014 220 808

(51) Int. Cl.
*H04L 29/06* (2006.01)
*H04L 9/32* (2006.01)
(Continued)

(52) U.S. Cl.
CPC ............ *H04L 9/3226* (2013.01); *G06F 21/35* (2013.01); *G06F 21/36* (2013.01); *H04L 9/085* (2013.01);
(Continued)

(58) Field of Classification Search
CPC ............. G06F 21/36; G06F 2221/2137; H04L 63/083; H04L 9/0841; H04L 9/0844; H04L 9/3226
See application file for complete search history.

(56) References Cited

U.S. PATENT DOCUMENTS

| 8,407,463 | B2 | 3/2013 | Ghirardi | |
|---|---|---|---|---|
| 2010/0275010 | A1 * | 10/2010 | Ghirardi | ................. G06F 21/35 713/155 |

(Continued)

FOREIGN PATENT DOCUMENTS

| CN | 102243714 A | 11/2011 |
|---|---|---|
| CN | 103001975 A | 3/2013 |

(Continued)

OTHER PUBLICATIONS

German Office Action for related German Application No. 10 2014 220 808.4 dated Dec. 16, 2015, with English Translation.
(Continued)

*Primary Examiner* — Dao Q Ho
(74) *Attorney, Agent, or Firm* — Lempia Summerfield Katz LLC

(57) ABSTRACT

The invention relates to a method for logging a service technician into an electrical device (20), comprising the following steps: production (3, 4) of a secret key (SKY) as an encrypted login password (LPW) by the electrical device (20), displaying (5) of the secret key (SKY) on a display unit (23) of the electrical device (20) as a QR code (QRC), optical sensing (6) of the QR code (QRC) by means of a mobile device (22), decryption (9) of the login password (LPW) from the secret key (SKY) of the sensed QR code (QRC) by the mobile device (22), displaying of the login password (LPW) on a screen unit (24) of the mobile device (22), entering of the login password (LPW) into the electrical device (20) by the service technician, comparison (10)

(Continued)

of the entered login password (LPW) with the produced login password (LPW) by the electrical device (20), release of the login by the electrical device (20) if the two login passwords (LPW) match. The invention further relates to an associated apparatus. The advantage of the invention lies in the combination of the high strength of the cryptographic security with the user friendliness of the QR code and of the relatively short login password to be entered.

13 Claims, 2 Drawing Sheets

(51) Int. Cl.

| | | |
|---|---|---|
| *G06F 21/35* | (2013.01) | |
| *G06F 21/36* | (2013.01) | |
| *H04L 9/08* | (2006.01) | |
| *H04L 9/14* | (2006.01) | |
| *H04L 9/30* | (2006.01) | |
| *G16H 40/40* | (2018.01) | |
| *G16H 40/63* | (2018.01) | |

(52) U.S. Cl.
CPC .......... *H04L 9/0841* (2013.01); *H04L 9/0844* (2013.01); *H04L 9/0863* (2013.01); *H04L 9/14* (2013.01); *H04L 9/3066* (2013.01); *H04L 9/3228* (2013.01); *H04L 63/083* (2013.01); *G06F 2221/2137* (2013.01); *G16H 40/40* (2018.01); *G16H 40/63* (2018.01); *H04L 2209/80* (2013.01); *H04L 2209/88* (2013.01)

(56) References Cited

U.S. PATENT DOCUMENTS

| | | | |
|---|---|---|---|
| 2014/0237252 A1 | 8/2014 | Hursti | |
| 2014/0337634 A1* | 11/2014 | Starner | ................ H04L 9/3231 |
| | | | 713/186 |

FOREIGN PATENT DOCUMENTS

| | | |
|---|---|---|
| CN | 103023919 A | 4/2013 |
| EP | 2493112A1 A1 | 8/2012 |
| EP | 2677681 A1 | 12/2013 |
| EP | 2220840B1 B1 | 1/2014 |
| WO | WO2009056897 A1 | 5/2009 |
| WO | WO2012116444 A | 9/2012 |

OTHER PUBLICATIONS

PCT International Search Report and Written Opinion of the International Searching Authority dated Dec. 17, 2015 for corresponding PCT/EP2015/073532.
European Search Report for European Patent Application No. 15781901.2-1213 dated Apr. 30, 2018.
Chinese Office Action for Chinese Application No. 201580055853.8 dated Jan. 4, 2019.

* cited by examiner

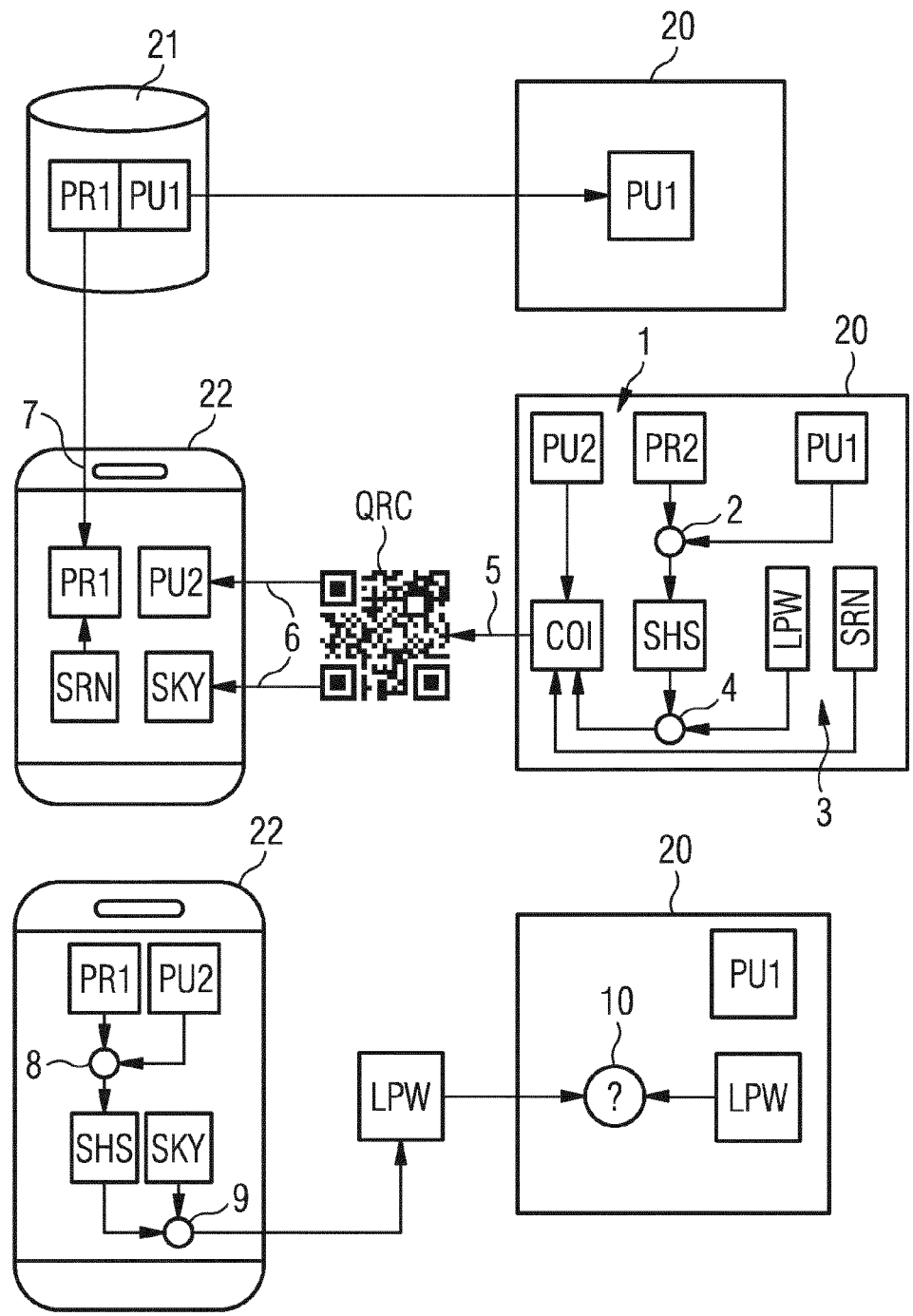

METHOD AND APPARATUS FOR LOGGING INTO MEDICAL DEVICES

CROSS REFERENCE TO RELATED APPLICATIONS

This application is the National Stage of International Application No. PCT/EP2015/073532, filed Oct. 12, 2015, which claims the benefit of German Patent Application No. 10 2014 220 808.4, filed Oct. 14, 2014. The entire contents of these documents are hereby incorporated herein by reference.

FIELD

Embodiments relate to a method and to an apparatus for logging a service technician into an electrical device such as a medical device.

BACKGROUND

Utilization of the service software of an electrical device (e.g., of a medical device) may be restricted to authorized persons. A symmetrical encryption method has been used in which various features of the medical device are combined with a secret. From this, a license key is generated. The secret may be discovered in relevant internet circles, or the license keys may become available on the black market.

Protective methods for preventing or impeding fraud may be used. In the public/private key method based on digital certificates, a handshake or a challenge/response method may be used. The establishment of a public key infrastructure (PKI) has a regular certificate update due to elapsing validities. The input of static key information uses a great length of key in order to reduce brute force attacks. Long key lengths are user-unfriendly. Time based one time passwords have a drawback of presupposing a time synchronization or an on-line connection.

SUMMARY

In an embodiment, a method and an apparatus provide that use of a service software of an electrical device is only possible for authorized persons.

In an embodiment, the method and the associated apparatus include generating a temporary login password and temporary key material, the validity of which is limited to the respective login process. In combination with a public/private pair of keys that is generated during the production of the system and the private key of which is stored and protected on a mobile device (e.g., on a smartphone of a service technician), the temporary login password may be kept short in a user-friendly manner. The transmission of information between the electrical device and the mobile device takes place via a QR code and is, therefore, also user-friendly.

For the pairs of public/private keys, the known elliptic curve crypto methods may be used. To generate a temporary common secret that is used for encrypting the login password, the established Diffie-Hellman key exchange method may be used.

Embodiments provide a method for logging a service technician into an electrical device. A secret key is generated by the electrical device as an encrypted login password. The secret key is represented on a display unit of the electrical device as a QR code. The QR code is detected optically with the aid of a mobile device. The login password is decrypted by the mobile device from the secret key of the detected QR code. The login password is displayed on a screen unit of the mobile device. The login password is input into the electrical device by the service technician. The login password input is compared with the generated login password by the electrical device. The login is released by the electrical device when the two login passwords match.

Embodiments provide a combination of a high strength of the cryptographic protection with a user-friendliness of the QR code and a relatively short login password to be input. Embodiments provide a possibility of combining device specific keys having a greater length and user-friendly login passwords by using smartphone technologies.

In an embodiment, a first public key and an associated first private key are generated before the delivery of the electrical device in a service center. The first private key may be stored in the service center, and the first public key may be installed on the electrical device.

In a further embodiment, the encryption and the decryption of the login password may take place with the aid of a shared secret.

In a further embodiment, the shared secret may be calculated or generated, respectively, by an elliptic-curve Diffie-Hellman key exchange method.

In a further embodiment, the shared secret may be determined in the mobile device with the aid of a second public key generated in the electrical device and the first private key. The first private key may be stored in a secure storage area of the mobile device.

In a further embodiment, the QR code may contain a combination of the secret key, the second public key, and a material/serial number of the electrical device.

In a further embodiment, the mobile device may allocate the first private key belonging to the electrical device using the material/serial number.

The login password may be valid in a manner restricted in time.

An embodiment provides an apparatus for logging a service technician into an electrical device. The apparatus includes a mobile device and the electrical device. The electrical device and the mobile device are configured (e.g., programmed) to carry out a method according to an embodiment.

In a further embodiment, the apparatus further includes a service center. The service center, the electrical device and the mobile device are configured (e.g., programmed) to carry out a method according to an embodiment.

The service center, the electrical device and the mobile device may include an electronic computing unit (e.g., a processor) and a storage unit (e.g., a memory) for carrying out the method.

In a further embodiment, the mobile device may be a smartphone or a tablet computer and the electrical device may be a medical device.

The scope of the present invention is defined solely by the appended claims and is not affected to any degree by the statements within this summary. The present embodiments may obviate one or more of the drawbacks or limitations in the related art.

BRIEF DESCRIPTION OF THE FIGURES

FIG. 1 depicts an example apparatus for logging in.
FIG. 2 depicts a flowchart of a method of logging in.

DETAILED DESCRIPTION

In an embodiment, a medical device (e.g., for a computer tomograph or a magnetic resonance tomograph) and a smartphone as mobile device may be used. The protection of applications having symmetric keys uses local storage of a key on the medical device. If, however, too many medical devices use the same key, the attractiveness for a fraudulent attack is increased.

Figure 1:
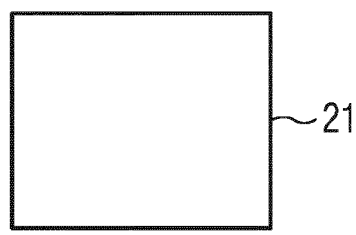
Figure 1:
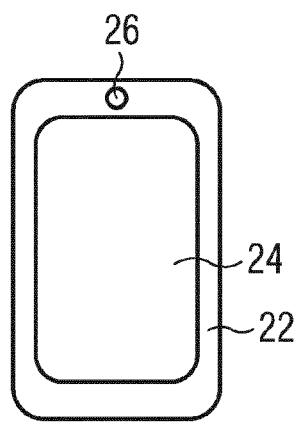
Figure 1:
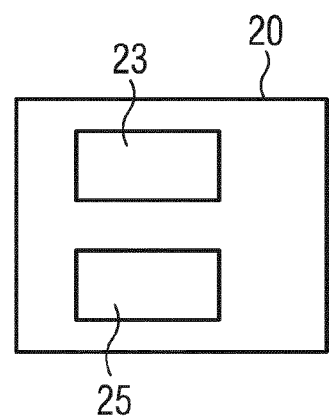

FIG. 1 depicts a block diagram of an apparatus for a secure login on a medical device 20. Apart from the medical device 20, the apparatus includes a service center 21 that is located remotely from the medical device 20, and a smartphone 22.

The apparatus provides a login method for the medical device 20 in order to implement an application protection for the medical device 20 without neglecting user-friendliness. The login method is used, for example, during service. Medical devices 20 that are located geographically distributed after their delivery may be subjected to regular maintenance. In order to provide maintenance, a service technician may authenticate at the medical device 20.

In order to avoid storage of a private key on the medical device 20, a public/private key infrastructure is utilized. An elliptic curve Diffie-Hellman key exchange method may be used.

Before the delivery of the medical device 20, an elliptic curve public/private key pair (first public key PU1 and first private key PR1) is generated in the service center 21. The first private key PR1 remains in the service center 21, and the first public key PU1 is installed on the medical device 20 to be delivered.

Knowledge of the first private key PR1 is accepted as prerequisite for access to the medical device 20. The length of the first private key PR1 is sufficiently large to provide good protection against factorization. The first private key PR1 is too long, however, to be input locally by hand by a service technician.

The service technician has access to the smartphone 22 including a camera 26 and a service-specific login application. At the service time, a direct on-line connection of the smartphone 22 to the service center 21 may not be required. A prior synchronization of the smartphone 22 with a central database of the service center 21 may be used.

The functional sequence for generating a login password LPW includes the following acts. The service technician calls up the login mask of the medical device 20. The medical device 20 displays a QR code QRC on a display unit 23 and provides a password input field. The service technician starts the login application on the smartphone 22 and scans in the displayed QR code QRC with the camera 26. The login application of the smartphone 22 displays a, for example, 12-digit temporary login password LPW on a screen unit 24 of the smartphone 22. The service technician inputs with the aid of an input unit 25, for example with a keyboard, the temporary login password LPW in the login mask of the medical device 20. The login is granted.

FIG. 2 depicts a flowchart of the login using the apparatus of FIG. 1. With the call-up of the login mask at the medical device 20, the following acts are performed in the background. At act 1, the medical device 20 generates a volatile pair of public/private keys (e.g., "ephemeral", second public key PU2 and second private key PR2). From the second private key PR2 of the volatile pair of keys and the first public key PU1 of the medical device that was created at the time of delivery, a common secret SHS ("shared secret") is generated at act 2.

At act 3, the medical device 20 generates a random and, for example, 12-digit sequence of numbers/letters (e.g., login password LPW) that may be input at a later time by the service technician. Internally, an expiry date that specifies for how long the medical device 20 accepts the temporary login password LPW as a login is defined. A lower number of digits optionally may be used if, for example, the time window is correspondingly reduced.

At act 4, the login password LPW is encrypted with a symmetric algorithm and the shared secret SHS to form the secret key SKY. To increase security, the secret key SKY may be hashed before the secret key SKY is used as secret key SKY in order to eliminate weak bits (e.g., bits that may be predicted with limited effort) (ECIES). The secret key SKY is Base64-coded and combined with the volatile second public key PU2 and the material/serial number SRN of the medical device 20 to form the combined information COI.

The combined information COI of the three information items obtained in act 4 is presented as QR code QRC on the display unit 23 of the medical device 20. The two public keys PU1 and PU2 and the secret key SKY (e.g., the encrypted login password LPW) may be publicly known at a current time. All other information (e.g., private keys PR1 and PR2, shared secret SHS and login password LPW) may be located in the main memory of the medical device 20, in the service center 21, or in the smartphone 22.

In the next act 6, the service technician, using the smartphone 22, scans in the QR code QRC from the display unit 23 using the camera 26 of the smartphone 22. The smartphone 22 then has the information for decrypting the login password LPW. At act 7, with the material/serial number SRN, the matching first private key PK1 of the medical device 20 is loaded from the smartphone 22 internal memory area or with an available mobile radio link, called up directly from the service center 21 via a secure transmission channel.

At Act 8, the identical shared secret SHS is calculated from the second public key PU2 and the first private key PKI, now available, of the medical device 20. Using the shared secret SHS, at act 9, the smartphone 22 decodes the encrypted secret key SKY to form the login password LPW and displays the encrypted secret key SKY on the screen unit 24 of the smartphone 22.

After input of the login password LPW into the medical device 20, the medical device 20 compares at act 10 the login password LPW input with the stored login password LPW and determines if the login is valid. In the case of a match, the service technician may access a protected application (e.g., a maintenance software).

Attack scenarios and possible countermeasures are described for the medical device 22. Due to the transmission of the first private key PR1 of the electrical device 20 to the mobile device 22 of the service technician, an increased risk exists when the mobile device 22 is stolen. Depending on the protection of the mobile device 22 (for example an unlocking code or remote wipe), the first private key PR1 may be identified an attacker. In the example, only those electrical devices 20 would be affected for which the first private keys PR1 were stored on the mobile device 22.

As a countermeasure, the maximum number of the first private keys PR1 stored in the mobile device 22 may be restricted. If an on-line link may be provided at any time, an advance synchronization of the mobile device 22 before action of the service technician may be omitted or the maximum number of stored first private keys PR1 may be set to be very low. The application may mandatorily demand a starting password.

The hazard of man-in-the-middle attacks does not exist due to the static factory keys (generated in the service center) and the visual link during the exchange of messages between the electrical device 20 and the mobile device 22.

An attacker in the field may call up the login page on the electrical device 20 at any time and scan the QR code QRC. Brute force attacks on the cryptographic methods used may be extremely expensive in the case of Diffie-Hellman key exchange methods with keys of sufficient length. As a countermeasure, sufficiently large key lengths are used, the publicly made secret key SKY of which may be decoded in Base64 coding as QR code QRC.

The password field may also be checked out by brute force. With password lengths of 6-12 characters, a brute force attack may succeed faster than an attack on the ECDHE method. As a countermeasure, long login passwords LPW may be used that are still reasonable for a manual input by the service technician. Furthermore, blockage of the access after a number of false attempts into the application to be protected may be used. The protection may be installed either with a time limit (for example, with a progressive duration of blockage) or in such a manner that only a remote administration may cancel the blockage.

Since both the temporary pair of keys and the login password LPW are newly generated randomly every time, the security may depend on the quality of the random number generator. If an attacker copies the password input, the attacker might reuse the password. As a countermeasure, tried algorithms are used for generating pseudorandom numbers. In addition, the electrical device 20 may accept a generated login password LPW only for a limited period of time. The last login password LPW generated may become immediately invalid after a successful login. The two elliptical curves supported in current browsers (prime256v1 and secp384r1) may be used. With regard to the Central American institutions (e.g. NIST) on the standardization bodies and that both abovementioned curves are curves that meet the NSA Suite B security requirements, alternative curves may be used, for example curve 25519.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for logging a service technician into an electrical device, the method comprising:
    generating, prior to delivery of the electrical device in a service center, a first public key and a first private key;
    storing the first private key in a mobile device with a serial number of the electrical device;
    installing the first public key on the electrical device;
    generating, by the electrical device, a second public key and a second private key;
    generating, by the electrical device, a shared secret from the second private key and the first public key;
    generating, by the electrical device, a temporary login password;
    encrypting, by the electrical device, the temporary login password using a symmetric algorithm and the shared secret;
    generating, by the electrical device, a QR code comprising the second public key, a serial number of the electrical device, and the encrypted temporary login password;
    displaying, by the electrical device, the QR code;
    detecting optically, by the mobile device, the QR code;
    determining, by the mobile device, the shared secret using the second public key and the first private key;
    decrypting the login password by the mobile device using the shared secret;
    displaying the login password on a display of the mobile device;
    inputting the login password into the electrical device;
    comparing, by the electrical device, the inputted login password with the temporary login password; and
    releasing the login by the electrical device when the inputted login password and the temporary login password match.

2. The method of claim 1, wherein the shared secret is generated by an elliptic curve Diffie-Hellman key exchange method.

3. The method of claim 1, further comprising:
    allocating, by the mobile device, the first private key for the electrical device using the material/serial number.

4. The method of claim 1, wherein the login password is valid in a manner restricted in time.

5. The method of claim 1, wherein the shared secret is generated by an elliptic curve Diffie-Hellman key exchange method.

6. The method of claim 1, wherein the first private key transmitted to the mobile device from the service center via a secure transmission channel.

7. An apparatus comprising:
    an electrical device configured to store a first public key, generate a second public using the first public key, generate a second private key, generate a shared secret from the second private key and the first public key, generate a temporary login password, encrypt the temporary login password using a symmetric algorithm and the shared secret, and generate a QR code comprising the second public key, a serial number of the electrical device, and the encrypted temporary login password, and display the QR code;
    a mobile device configured to store the first private key and the first public key, optically detect the QR code, decrypt the encrypted login password using the shared secret, and display the login password; and
    a service center configured, prior to delivery of the electrical device, to generate the first public key and the first private key, wherein the first public key and first private key are stored at the service center and the first private key is stored on an electrical device;
    wherein the electrical device operable to be logged onto when a service technician enters the login password at the electrical device.

8. The apparatus of claim 7, wherein the service center is configured to transmit the first private key to the mobile device via a secure transmission channel.

9. The apparatus of claim 7, wherein the mobile device is a smartphone or a tablet computer, and the electrical device is a medical device.

10. The apparatus of claim 7, wherein the shared secret is generated using an elliptic curve Diffie-Hellman key exchange method.

11. The apparatus of claim 7, wherein the QR code contains a combination of the secret key, the second public key, and a serial number of the electrical device.

12. The apparatus of claim 11, wherein the mobile device is further configured to allocate the first private key for the electrical device using the serial number.

13. The apparatus of claim 7, wherein the login password is valid in a manner restricted in time.

* * * * *